US011883539B2

(12) United States Patent
Liu (10) Patent No.: US 11,883,539 B2
(45) Date of Patent: *Jan. 30, 2024

(54) PHARMACEUTICAL COMPOSITIONS OF BERBERINE WITH EPA AND DHA, AND METHODS THEREOF (71) Applicant: SHENZHEN HIGHTIDE BIOPHARMACEUTICAL, LTD., Shenzhen (CN)

(72) Inventor: Liping Liu, Manassas, VA (US)

(73) Assignee: Shenzhen HighTide Biopharmaceutical, Ltd., Shenzhen (CN)

(*) Notice: Subject to any disclaimer, the term of this patent is extended or adjusted under 35 U.S.C. 154(b) by 0 days.

This patent is subject to a terminal disclaimer.

(21) Appl. No.: 17/744,685

(22) Filed: May 15, 2022

(65) Prior Publication Data

US 2022/0296528 A1    Sep. 22, 2022

Related U.S. Application Data (60) Continuation of application No. 16/857,798, filed on Apr. 24, 2020, now Pat. No. 11,369,573, which is a
(Continued)

(51) Int. Cl.
A61K 9/48 (2006.01)
A61K 31/202 (2006.01)
(Continued)

(52) U.S. Cl.
CPC .............. A61K 9/48 (2013.01); A61K 31/202 (2013.01); A61K 31/232 (2013.01);
(Continued)

(58) Field of Classification Search
None
See application file for complete search history.

(56) References Cited

U.S. PATENT DOCUMENTS

2013/0273175 A1* 10/2013 Finley ................ A61K 36/9066
424/635
2016/0235822 A1* 8/2016 Holstein .............. A61K 31/519

FOREIGN PATENT DOCUMENTS

WO    WO-2015034984 A1 *  3/2015  ............. A23L 33/12

OTHER PUBLICATIONS

SBH, "Fish Oil: EE vs. TG omega-3s—which is better?" ([Retrieved from on-line website: https://web.archive.org/web/20151210060456/http://www.sciencebasedhealth.com:80/Fish-Oil-EE-vs-TG-omega-3s-which-is-better-W119.aspx, Nov. 2014]) ( Year: 2014).*

* cited by examiner

Primary Examiner — Kyung S Chang
(74) Attorney, Agent, or Firm — Milstein Zhang & Wu LLC (57) ABSTRACT The invention provides various novel compositions of berberine in combination with pharmacologically active EPA and DHA, and related methods of their use in treating various diseases or disorders. The pharmaceutical compositions of the invention are useful in treating and/or preventing various diseases or disorders, including metabolic diseases or disorders such as dyslipidemia, hyperglycemia, hypertriglyceridemia, hyperlipidemia, diabetic dyslipidemia, diabetic hyperlipidemia, dyslipidemia in statin-intolerance patients, diabetes, diabetic complications, hypercholesterolemia, or obesity. Additionally, the pharmaceutical compositions of the invention are useful in treating and/or preventing atherosclerosis, heart diseases, neurodegenerative diseases, inflammation, cancers, as well as various liver diseases or disorders, such as fatty liver, non-alcoholic fatty liver disease, non-alcoholic steatohepatitis, cholestatic liver diseases or graft-versus-host disease of the liver. Furthermore, the pharmaceutical compositions of the invention are
(Continued)

Glucose and lipid regulating mechanisms of action of BBR useful in improving liver functions in chronic viral associated liver diseases and alcohol-related liver diseases.

7 Claims, 5 Drawing Sheets

Related U.S. Application Data division of application No. 15/384,943, filed on Dec. 20, 2016, now abandoned, which is a continuation-in-part of application No. PCT/CN2016/105294, filed on Nov. 10, 2016.

(60) Provisional application No. 62/254,739, filed on Nov. 13, 2015.

(51) Int. Cl.
*A61K 31/232* (2006.01)
*A61K 31/4745* (2006.01)
*A61K 45/06* (2006.01)
*A61P 3/00* (2006.01)

(52) U.S. Cl.
CPC .......... *A61K 31/4745* (2013.01); *A61K 45/06* (2013.01); *A61P 3/00* (2018.01)

FIG. 1. Glucose and lipid regulating mechanisms of action of BBR

FIG. 2. BBR Bioavailability Improvement of $C_{max}$

FIG. 3. BBR Bioavailability Improvement of $AUC_{(0-t)}$

For the BBR + EPA/DHA groups, BBR•HCl dosage remained at 100 mg/kg which is consistent with the BBR group. For EPA/DHA administration alone with the dose of 100mg/kg, the exposure level of EPA was equivalent to vehicle control.

FIG. 4. EPA Bioavailability Improvement

FIG. 5. The plots of BBR plasma concentrations versus time curves in dogs

PHARMACEUTICAL COMPOSITIONS OF BERBERINE WITH EPA AND DHA, AND METHODS THEREOF

PRIORITY CLAIMS AND RELATED PATENT APPLICATIONS

This application is a continuation of and claims the benefit of priority to U.S. Ser. No. 16/857,798, filed Apr. 24, 2020, which is a divisional of and claims the benefit of priority to U.S. Ser. No. 15/384,943, filed Dec. 20, 2016, which claims priority to PCT/CN2016/105294, filed Nov. 10, 2016, which claims priority to U.S. Provisional Application No. 62/254,739, filed Nov. 13, 2015, the entire content of each of which is incorporated herein by reference.

TECHNICAL FIELD OF THE INVENTION

The invention generally relates to novel compositions and methods of preparation and therapeutic use thereof. In particular, the invention relates to novel pharmaceutical compositions of berberine in combination with omega-3 fatty acids, e.g., eicosapentaenoic acid (EPA) and/or docosahexaenoic acid (DHA), or esters thereof, and methods of their use. The pharmaceutical compositions of the invention are useful in treating and/or preventing various diseases or disorders, including metabolic diseases or disorders such as dyslipidemia, hyperglycemia, hypertriglyceridemia, hyperlipidemia, diabetic dyslipidemia, diabetic hyperlipidemia dyslipidemia in statin-intolerance patients, diabetes, diabetic complications, hypercholesterolemia, or obesity. Additionally, the pharmaceutical compositions of the invention are useful in treating and/or preventing atherosclerosis, heart diseases, neurodegenerative diseases, inflammation, cancers, as well as various liver diseases or disorders, such as fatty liver, non-alcoholic fatty liver disease, non-alcoholic steatohepatitis, cholestatic liver diseases or graft-versus-host disease of the liver. Furthermore, the pharmaceutical compositions of the invention are useful in improving liver functions in chronic viral associated liver diseases and alcohol-related liver diseases.

BACKGROUND OF THE INVENTION

Dyslipidemia is a disorder of lipoprotein metabolism, including lipoprotein overproduction (hyperlipidemia) or deficiency. Dyslipidemias may be manifested by elevation of the total cholesterol, the "bad" low-density lipoprotein cholesterol and the triglyceride concentrations, and a decrease in the "good" high-density lipoprotein cholesterol concentration in the blood. Dyslipidemia comes under consideration in many situations including diabetes, a common cause of dyslipidemia.

Hyperlipidemia (or hyperlipoproteinemia) is the most common form of dyslipidemia. It is characterized by abnormally elevated levels of any or all lipids and/or lipoproteins in the blood. Diagnosis is by measuring plasma levels of total cholesterol, triglyceride, and individual lipoproteins. Treatment involves dietary changes, exercise, and lipid-lowering drugs. Hyperlipidemias are divided into primary and secondary subtypes. Primary hyperlipidemia is usually due to genetic causes (such as a mutation in a receptor protein), while secondary hyperlipidemia arises due to other underlying causes such as diabetes. Lipid and lipoprotein abnormalities are regarded as a modifiable risk factor for cardiovascular disease due to their influence on atherosclerosis.

Hyperglycemia (or high blood sugar) is a condition characterized by an excessive amount of glucose circulates in the blood plasma. Hyperglycemia is a potentially serious condition if not treated in time since ketoacidosis, a life-threatening condition, could occur and needs immediate treatment. Chronic hyperglycemia causes injuries to the heart and is strongly associated with heart attacks and death in subjects with no coronary heart disease or history of heart failure.

Diabetes mellitus (or diabetes) is a disorder of metabolism. It has become pandemic with an estimate of over 300 million people worldwide living with diabetes today. Without effective prevention, this number will grow up to 500 million by 2030. There are three main types of diabetes: type 1 diabetes, type 2 diabetes, and gestational diabetes. Among them, type 2 diabetes, is the most common form of diabetes accounting for 90-95% of cases. Type 2 diabetes is characterized by impaired insulin secretion, increased hepatic glucose production, and decreased response of peripheral tissues to insulin, i.e., insulin resistance. Many therapeutic treatments are available for the management of type 2 diabetes, but they are often accompanied by various side effects. An optimal therapy should be safe and include early initiation of combination drugs with complimentary mechanisms of action.

Despite persistent efforts and meaningful progress over the past decades in the understanding and management of diabetes, people with diabetes continue to have an increased risk of, and many do suffer from, a number of serious complications inflicting the heart and blood vessels, eyes, kidneys, and nerves due to high blood glucose, high cholesterol, and high blood pressure. Cardiovascular diseases are the most common cause of death in people with diabetes. Diabetic nephropathy caused by damages to small blood vessels in the kidney leads to decreased kidney function or kidney failure altogether. Diabetic neuropathy is caused by damages to the nerves throughout the body when blood glucose level and blood pressure are too high. Most people with diabetes develop diabetic retinopathy causing reduced vision or blindness. Consistently high levels of blood glucose, together with high blood pressure and high cholesterol, are the main causes of diabetic retinopathy. Despite the development of a number of anti-diabetic agents, there are significant unmet needs for therapeutics that can be used effectively for the treatment and management of diabetic complications.

Metabolic syndrome is a term that refers to a group of risk factors that occur together (e.g., abdominal (central) obesity, elevated blood pressure, elevated fasting plasma glucose, high serum triglycerides, and low high-density cholesterol (HDL) levels). Metabolic syndrome has been demonstrated to increase the risk of developing cardiovascular diseases, particularly heart failure, and diabetes. Studies have estimated that the prevalence of metabolic syndromes in the US to be around 34% in the adult population. While therapeutics are available, the first line treatment is change of lifestyle. High-dose statins, recommended to reduce cardiovascular risks, have been linked to higher progression to diabetes, especially in patients with metabolic syndrome.

Cardiovascular disease (CV), often used interchangeably with the term 'heart disease', refers to a range of conditions that affect the heart such as coronary artery disease, arrhythmias, congestive heart failure, cerebrovascular disease etc. Many forms of CV can be prevented or treated with healthy lifestyle choices, by controlling conditions such as atherosclerosis, high blood pressure, diabetes or obesity with a verity of medicines such as antiplatelet drugs, anticoagulants, digitalis, angiotensin converting enzyme (ACE) inhibitors, beta blockers, and LDL cholesterol-lowering agents etc. Due to the comorbidity, patients often need to take multiple medicines, and it would be desirable if one pill can target multiple abnormalities.

With demonstrated ability to prevent cardiovascular disease, statins are among one of the most widely prescribed medications. Although statins are generally well tolerated, statin intolerance occurs in some patients and requires careful consideration. In addition, patients are sometimes concerned about the potential risk of statins causing diabetes mellitus, cancer, and memory loss and often question whether they should continue with their medication. For statin-intolerant patients, non-statin LDL-C-lowering drugs can be used; however, till the PCSK9 inhibitors are approved, none of the approved drugs has been nearly as effective as statins. Developing alternative and effective therapeutics for these patients is much needed.

Neurodegenerative disease is an umbrella term for a range of conditions that primarily affect the neurons in the human brain. Neurons are the building blocks of the nervous system that includes the brain and spinal cord. Neurons normally don't reproduce or replace themselves when they become damaged or die. Examples of neurodegenerative diseases include Parkinson's, Alzheimer's, and Huntington's disease. Neurodegenerative diseases are incurable and debilitating conditions that result in progressive degeneration and/or death of nerve cells. The unmet medical needs for neurodegenerative diseases desperately call for the development of effective therapeutics.

Cancer is a group of diseases involving abnormal cell growth with the potential to invade or spread to other parts of the body. In 2012, about 14 million new cases of cancer occurred globally. The most common types of cancer include lung cancer, prostate cancer, colorectal cancer and stomach cancer for men, and breast cancer, colorectal cancer, lung cancer and cervical cancer for women. While many treatment options for cancer exist, including surgery, chemotherapy, radiation therapy, hormonal therapy, targeted therapy and palliative care, cancer remains a top health threat and is responsible for about 15% of all human deaths.

Fatty liver is a reversible condition wherein large vacuoles of triglyceride fat accumulate in liver cells via the process of steatosis. Despite having multiple causes, fatty liver can be considered a single disease that occurs worldwide in those with excessive alcohol intake and the obese. Non-alcoholic fatty liver disease (NAFLD) is a form of fatty liver diseases that occurs when excessive fat is deposited in the liver of patients without excessive alcohol intake. NAFLD is generally recognized to be associated with metabolic syndrome such as insulin resistance, hypertension and obesity. NAFLD affects about a third of the adult population in developed countries. Non-alcoholic steatohepatitis (NASH) is the most extreme form of NAFLD with chronic inflammation that can lead to progressive fibrosis (scarring), cirrhosis, and eventual liver failure and death. NASH resembles alcoholic liver disease, but occurs in people who drink little or no alcohol. A major feature of NASH is fat in the liver, along with inflammation and damage. Most people with NASH, an often "silent" liver disease, feel well and are not aware that they have a liver problem. Nevertheless, NASH can be severe and can lead to cirrhosis, when the liver is permanently damaged and scarred and no longer work properly.

Currently, there are no drugs approved for the treatment of NASH, which occurs in about a quarter of patients with NAFLD. The current standard of care for NASH involves weight loss and increased physical activities. NASH affects 2-5% of Americans and is becoming more common, possibly because of the greater number of Americans with obesity. In the past 10 years, the rate of obesity has doubled in adults and tripled in children.

The therapeutics and methods currently available for the management of diseases or disorders such as diabetes, diabetic complications, dyslipidemia, obesity, metabolic syndromes, pre-diabetes, Heart diseases, neurodegenerative diseases, NAFLD, NASH, muscle atrophy, inflammation and cancers are suboptimal. There remains an ongoing and urgent need for novel and improved therapeutics and methods to treat such diseases or disorders.

SUMMARY OF THE INVENTION

The invention is based in part on novel pharmaceutical compositions of berberine in combination with omega-3 fatty acids, e.g., EPA and/or DHA, or esters thereof, and related methods of their use in treating and/or preventing various diseases or disorders.

The pharmaceutical compositions of the invention can be utilized to treat various diseases or disorders including lipid and glucose diseases or disorders such as dyslipidemia, hyperglycemia, hypertriglyceridemia, hyperlipidemia, diabetic dyslipidemia, diabetic hyperlipidemia, dyslipidemia in statin-intolerance patients, diabetes, diabetic complications, hypercholesterolemia, obesity, metabolic syndromes, prediabetes, heart diseases, neurodegenerative diseases, inflammation, and cancers as well as various liver diseases or disorders, such as fatty liver, non-alcoholic fatty liver disease, non-alcoholic steatohepatitis, cholestatic liver diseases or graft-versus-host disease of the liver.

In one aspect, the invention generally relates to a pharmaceutical composition that includes: (a) berberine, or a pharmaceutically acceptable salt thereof; (b) one or both of eicosapentaenoic acid, or a pharmaceutically acceptable ester thereof, and docosahexaenoic acid, or a pharmaceutically acceptable ester thereof; and (c) optionally a pharmaceutically acceptable excipient, carrier, or diluent. The berberine, or a pharmaceutically acceptable salt thereof, and the one or both of eicosapentaenoic acid, or a pharmaceutically acceptable ester thereof, and docosahexaenoic acid, or a pharmaceutically acceptable ester thereof, are present in amounts that, when administered to a subject, are sufficient to treat, prevent, or reduce one or more diseases or disorders selected from metabolic diseases or disorders, heart diseases or disorders, neurodegenerative diseases or disorders, inflammation, cancers and liver diseases or disorders, or a related condition thereof in a mammal, including a human.

In another aspect, the invention generally relates to a unit dosage form of a pharmaceutical composition comprising BBR ranging from about 100 mg to about 300 mg and EPA/DHA ranging from about 100 mg to about 800 mg EPA/DHA.

In yet another aspect, the invention generally relates to a method for treating, reducing, or preventing a disease or disorder. The method includes: administering to a subject in need thereof a pharmaceutical composition comprising (a) berberine, in a therapeutically effective amount; (b) one or both of eicosapentaenoic acid, or a pharmaceutically acceptable ester thereof, and docosahexaenoic acid, or a pharmaceutically acceptable ester thereof, in therapeutically effective amounts, and (c) optionally a pharmaceutically acceptable excipient, carrier, or diluent. The disease or disorder is selected from metabolic diseases or disorders, heart diseases or disorders, neurodegenerative diseases or disorders, inflammation, cancers and liver diseases or disorders, or a related condition thereof in a mammal, including a human.

In yet another aspect, the invention generally relates to a kit including: (i) berberine, or a pharmaceutically acceptable salt thereof; (ii) one or both of eicosapentaenoic acid, or a pharmaceutically acceptable ester thereof, and docosahexaenoic acid, or a pharmaceutically acceptable ester thereof; (iii) one or more agent(s) selected from the group consisting of vitamin D, vitamin C, vitamin E, vitamin B12, vitamin A, benfotiamine, chromium picolinate and vanadium; and (iv) instructions for administering agents (i), (ii) and (iii) to a patient having or at risk of having one or more diseases or disorders selected from metabolic disorders, atherosclerosis, heart diseases, neurodegenerative diseases and liver diseases.

DEFINITIONS

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Given the benefit of this disclosure, one of ordinary skill in the art will appreciate that synthetic methods, as described herein, may utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by preferably readily available, non-toxic reagents that do not attack the other functional groups; the protecting group forms an easily separable derivative (more preferably without the generation of new stereogenic centers); and the protecting group has a minimum of additional functionality to avoid further sites of reaction. Oxygen, sulfur, nitrogen, and carbon protecting groups may be utilized. Examples of a variety of protecting groups can be found in Protective Groups in Organic Synthesis, Third Ed. Greene, T. W. and Wuts, P. G., Eds., John Wiley & Sons, New York: 1999.

It will be appreciated that the compounds, as described herein, may be substituted with any number of substituents or functional moieties. Throughout the specifications, groups and substituents thereof may be chosen to provide stable moieties and compounds.

As used herein, the term "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the term "treating, reducing, or preventing a disease or disorder" refers to ameliorating such a condition before or after it has occurred. As compared with an equivalent untreated control, such reduction or degree of prevention is at least 5%, 10%, 20%, 40%, 50%, 60%, 80%, 90%, 95%, or 100% as measured by any standard technique.

As used herein, the term "pharmaceutically acceptable excipient, carrier, or diluent" refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the terms "isolated" or "purified" refer to a material that is substantially or essentially free from components that normally accompany it in its native state. Purity and homogeneity are typically determined using analytical chemistry techniques such as polyacrylamide gel electrophoresis or high performance liquid chromatography.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

As used herein, the "an amount sufficient" refers to the amount of a compound, alone or in combination with another therapeutic regimen, required to treat, prevent, or reduce a metabolic disorder such as diabetes in a clinically relevant manner. A sufficient amount of an active compound used to practice the present invention for therapeutic treatment of conditions caused by or contributing to diabetes varies depending upon the manner of administration, the age, body weight, and general health of the mammal or patient. Ultimately, the prescribers will decide the appropriate amount and dosage regimen. Additionally, an effective amount may be an amount of compound in the combination of the invention that is safe and efficacious in the treatment of a patient having a metabolic disorder such as diabetes over each agent alone as determined and approved by a regulatory authority (such as the U.S. Food and Drug Administration).

As used herein, the "low dosage" refers to at least 5% less (e.g., at least 10%, 20%, 50%, 80%, 90%, or even 95%) than the lowest standard recommended dosage of a particular compound formulated for a given route of administration for treatment of any human disease or condition. For example, a low dosage of an agent that reduces glucose levels and that is formulated for administration by inhalation will differ from a low dosage of the same agent formulated for oral administration.

As used herein, the "high dosage" is meant at least 5% (e.g., at least 10%, 20%, 50%, 100%, 200%, or even 300%) more than the highest standard recommended dosage of a particular compound for treatment of any human disease or condition.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

By isotopically-labeling the presently disclosed compounds, the compounds may be useful in drug and/or substrate tissue distribution assays. Tritiated ($^3H$) and carbon-14 ($^{14}C$) labeled compounds are particularly preferred for their ease of preparation and detectability. Further, substitution with heavier isotopes such as deuterium ($^2H$) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical salts, esters, and prodrugs thereof, can be prepared by any means known in the art.

Further, substitution of normally abundant hydrogen ($^1H$) with heavier isotopes such as deuterium can afford certain therapeutic advantages, e.g., resulting from improved absorption, distribution, metabolism and/or excretion (ADME) properties, creating drugs with improved efficacy, safety, and/or tolerability. Benefits may also be obtained from replacement of normally abundant $^{12}C$ with $^{13}C$. See, WO 2007/005643, WO 2007/005644, WO 2007/016361, and WO 2007/016431.

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure.

Solvates and polymorphs of the compounds of the invention are also contemplated herein. Solvates of the compounds of the present invention include, for example, hydrates.

Possible formulations include those suitable for oral, sublingual, buccal, parenteral (for example subcutaneous, intramuscular, or intravenous), rectal, topical including transdermal, intranasal and inhalation administration. Most suitable means of administration for a particular patient will depend on the nature and severity of the disease or condition being treated or the nature of the therapy being used and on the nature of the active compound.

DETAILED DESCRIPTION OF THE INVENTION

The invention provides various novel compositions of berberine in combination with omega-3 fatty acids, e.g., EPA and/or DHA, or esters thereof, and related methods of their use in treating and/or preventing various diseases or disorders.

A key feature of the invention is the unique and synergistic pharmacological effects and reduction of side effects given rise (1) by berberine, which increases the bioavailability and reduces the risk of certain side effects of EPA and/or DHA, or esters thereof, and (2) by EPA and/or DHA, or esters thereof, which significantly improves the bioavailability of berberine. The carefully chosen dosages of each of these agents in the pharmaceutical composition provide the optimized overall therapeutic benefits to patients. Thus, for the first time, a single pharmaceutical composition can effectively address two or more diseases and disorders, for examples, dyslipidemia and hyperglycemia.

Diseases and disorders that may be treated and/or prevented by the pharmaceutical compositions and methods disclosed herein include metabolic diseases or disorders such as dyslipidemia, hyperglycemia, hypertriglyceridemia, hyperlipidemia, diabetic dyslipidemia, diabetic hyperlipidemia, dyslipidemia in statin-intolerance patients, diabetes, diabetic complications, hypercholesterolemia, obesity, metabolic syndromes or pre-diabetes, heart diseases, neurodegenerative diseases, inflammation, and cancers as well as various liver diseases or disorders, such as fatty liver, non-alcoholic fatty liver disease, non-alcoholic steatohepatitis, cholestatic liver diseases or graft-versus-host disease of the liver. The compounds of this invention are also useful in improving liver functions in chronic viral associated liver diseases and alcohol-related liver diseases.

In one aspect, the invention generally relates to a pharmaceutical composition that includes: (a) berberine, or a pharmaceutically acceptable salt thereof; (b) one or both of eicosapentaenoic acid, or a pharmaceutically acceptable ester thereof, and docosahexaenoic acid, or a pharmaceutically acceptable ester thereof; and (c) optionally a pharmaceutically acceptable excipient, carrier, or diluent. The berberine, or a pharmaceutically acceptable salt thereof, and the one or both of eicosapentaenoic acid, or a pharmaceutically acceptable ester thereof, and docosahexaenoic acid, or a pharmaceutically acceptable ester thereof, are present in amounts that, when administered to a subject, are sufficient to treat, prevent, or reduce one or more diseases or disorders selected from metabolic diseases or disorders, heart diseases or disorders, neurodegenerative diseases or disorders, sarcopenia, muscle atrophy, inflammation, cancers and liver diseases or disorders, or a related condition thereof in a mammal, including a human.

Figure 1:
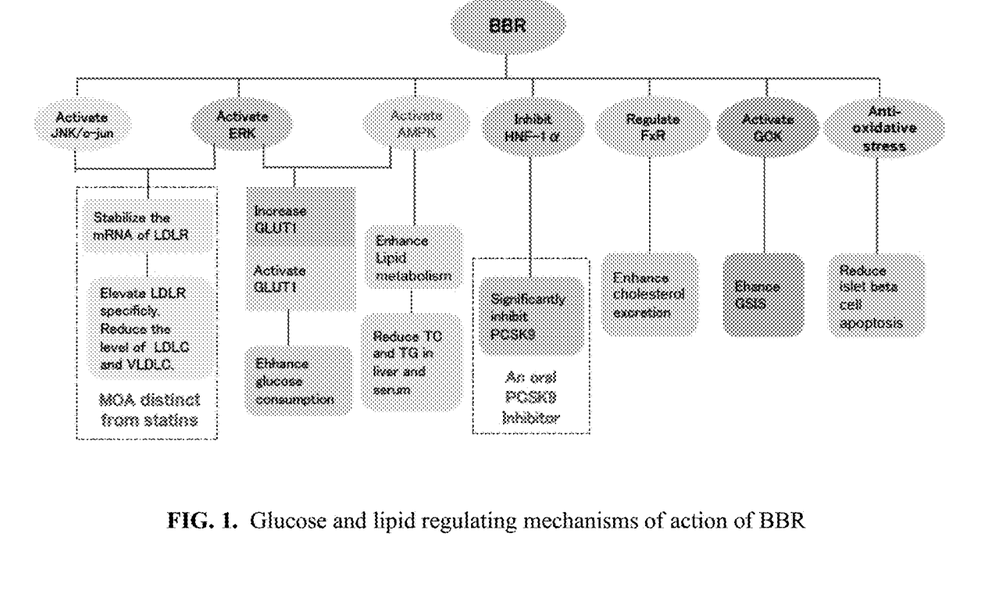
FIG. 1. Glucose and lipid regulating mechanisms of action of BBR.

Berberine (5,6-dihydro-9,10-dimethoxybenzo[g]-1,3-benzodioxolo[5,6-a]quinolizinium), an isoquinoline alkaloid isolated from Rhizoma Coptidis, has had a long history of medicinal use in China to treat various gastrointestinal diseases. Berberine is found in a variety of plants as *Berberis*, *Hydrastis canadensis*, *Xanthorhiza simplicissima*, *Phellodendron amurense*, *Coptis chinensis*, *Tinospora cordifolia*, *Argemone mexicana*, and *Eschscholzia californica*. In the past two decades, in vitro and in vivo studies have demonstrated the efficacy of berberine when used alone or as a combination for diabetes, dyslipidemia, cancer, neuroprotection and cardiovascular diseases. FIG. 1 shows various berberine's glucose and lipid regulating mechanisms of action.

Currently, berberine can be obtained commercially in the form of chloride, sulfate or tannate salt, with berberine hydrochloride having been used in almost all previous studies. The low bioavailability of berberine in the current available forms makes its applications for the treatment of chronic and systemic disease very challenging.

In certain embodiments, the pharmaceutical composition includes both of eicosapentaenoic acid, or a pharmaceutically acceptable ester thereof, and docosahexaenoic acid, or a pharmaceutically acceptable ester thereof.

Eicosapentaenoic acid (EPA or (5Z,8Z,11Z,14Z,17Z)-5,8,11,14,17-icosapentaenoic acid), and docosahexaenoic acid (DHA, 4Z,7Z,10Z,13Z,16Z,19Z)-docosa-4,7,10,13,16,19-hexaenoic acid), are two best-investigated omega-3 polyunsaturated fatty acids.

EPA is the active molecule in three FDA-approved antihypertriglyceridemic agents. It has been demonstrated that EPA and DHA can reduce free fatty acid and triglyceride synthesis and increase their disposal. Effects of EPA and DHA have also been demonstrated in reducing chronic inflammation, improving insulin resistance, maintaining heart and vascular health and reducing the risk of coronary heart disease. In addition to EPA and DHA, many more omega-3 fatty acids existed in nature with a range of therapeutic benefits, include but not limited to Docosapentaenoic acid (DPA), α-Linolenic acid (ALA), Eicosatrienoic acid (ETE) etc.

EPA

DHA

In certain embodiments, the pharmaceutical composition includes one of eicosapentaenoic acid, or a pharmaceutically acceptable ester thereof, and docosahexaenoic acid, or a pharmaceutically acceptable ester thereof.

Other omega-3 fatty acids may also be used here in addition to or in place of one or both of eicosapentaenoic acid and docosahexaenoic acid. For example, docosapentaenoic acid, α-Linolenic acid, eicosatrienoic acid, hexadecatrienoic acid, stearidonic acid, eicosatetraenoic acid, heneicosapentaenoic acid, tetracosapentaenoic acid and tetracosahexaenoic acid may be used in the pharmaceutical composition berberine in addition to or in place of EPA and DHA.

In certain embodiments, the pharmaceutical composition further includes one or more agents selected from the group consisting of vitamin D, vitamin C, vitamin E, vitamin B12, vitamin A, benfotiamine, chromium picolinate and vanadium.

Berberine

In certain embodiments, the disease or disorder is selected from lipid and glucose diseases or disorders.

In certain embodiments, the lipid and glucose disease or disorder is selected from dyslipidemia, hyperglycemia, hypertriglyceridemia, hyperlipidemia, diabetic dyslipidemia, diabetic hyperlipidemia, dyslipidemia in statin-intolerance patients.

In certain embodiments, the disease or disorder is type 1 or type 2 diabetes.

In certain embodiments, the disease or disorder is diabetic neuropathy, diabetic nephropathy, diabetic retinopathy, or macrovascular complications comprising heart attacks, strokes or insufficiency in blood flow to legs.

In certain embodiments, the disease or disorder is a heart disease or atherosclerosis.

In certain embodiments, the disease or disorder is a neurodegenerative disease.

In certain embodiments, the disease or disorder is selected from fatty liver, NAFLD and NASH.

In certain embodiments, the pharmaceutical composition includes a pharmaceutically acceptable excipient, carrier, or diluent.

In certain embodiments, the pharmaceutically acceptable ester of eicosapentaenoic acid is an ethyl ester of eicosapentaenoic acid and the pharmaceutically acceptable ester of docosahexaenoic acid is an ethyl ester of docosahexaenoic acid.

In certain embodiments, the pharmaceutical composition includes: (a) berberine, or a pharmaceutically acceptable salt thereof; (b) ethyl ester of eicosapentaenoic acid and ethyl ester of docosahexaenoic acid; and (c) a pharmaceutically acceptable excipient, carrier, or diluent.

As used herein, the term "pharmaceutically acceptable salt" refers to either a pharmaceutically acceptable acid addition salt or a pharmaceutically acceptable base addition salt of a currently disclosed compound that may be administered without any resultant substantial undesirable biological effect(s) or any resultant deleterious interaction(s) with any other component of a pharmaceutical composition in which it may be contained.

In certain embodiments, the pharmaceutically acceptable salt of berberine may be selected from salts of berberine cation with anions of chloride, bromide, iodide, sulfate, bisulfate, hemisulphate, nitrate, phosphate, acid phosphate, isonicotinate, acetate, lactate, salicylate, citrate, tartrate, pantothenate, bitartrate, ascorbate, succinate, tannate, maleate, gentisinate, fumarate, gluconate, glucaronate, saccharate, formate, benzoate, glutamate, etc.

In certain embodiments, the pharmaceutical composition includes BBR to EPA/DHA at a weight ratio of BBR to EPA/DHA from about 3:1 to about 1:8 (e.g., from about 3:1 to about 1:5, from about 3:1 to about 1:3, from about 3:1 to about 1:2, from about 3:1 to about 1:1, from about 3:1 to about 2:1, from about 2:1 to about 1:8, from about 2:1 to about 1:5, from about 2:1 to about 1:2, from about 2:1 to about 1:1, from about 1:1 to about 1:8, from about 1:1 to about 1:5, from about 1:1 to about 1:3, from about 3.33:1 to about 1:3, about 3:1, about 2:1, about 1:1, about 1:2, about 1:3).

As used herein, the term "pharmaceutically acceptable ester," refers to esters that hydrolyze in vivo and include those that break down readily in the human body to leave the parent compound or a salt thereof. Examples of particular esters include esters formed by an acid with a substituted or unsubstituted aliphatic alcohol (R—OH, wherein R is a $C_1$-$C_6$ alkyl group), for example, an ethyl ester or a propyl ester.

In another aspect, the invention generally relates to a unit dosage form of a pharmaceutical composition comprising BBR ranging from about 100 mg to about 300 mg (e.g., about 100 mg to about 250 mg, about 100 mg to about 200 mg, about 100 mg to about 150 mg, about 150 mg to about 300 mg, about 200 mg to about 300 mg, about 250 mg to about 300 mg, about 150 mg to about 250 mg) and EPA/DHA ranging from about 100 mg to about 800 mg EPA/DHA (e.g., about 100 mg to about 700 mg, about 100 mg to about 600 mg, about 100 mg to about 500 mg, about 100 mg to about 400 mg, about 100 mg to about 300 mg, about 100 mg to about 200 mg, about 200 mg to about 800 mg, about 300 mg to about 800 mg, about 400 mg to about 800 mg, about 500 mg to about 800 mg, about 600 mg to about 800 mg, about 700 mg to about 800 mg, about 250 mg to about 750 mg, about 500 mg to about 750 mg).

In yet another aspect, the invention generally relates to a method for treating, reducing, or preventing a disease or disorder. The method includes: administering to a subject in need thereof a pharmaceutical composition comprising (a) berberine, in a therapeutically effective amount; (b) one or both of eicosapentaenoic acid, or a pharmaceutically acceptable ester thereof, and docosahexaenoic acid, or a pharmaceutically acceptable ester thereof, in therapeutically effective amounts, and (c) optionally a pharmaceutically acceptable excipient, carrier, or diluent. The disease or disorder is selected from metabolic diseases or disorders, heart diseases or disorders, neurodegenerative diseases or disorders, sarcopenia, muscle atrophy, inflammation, cancers and liver diseases or disorders, or a related condition thereof in a mammal, including a human.

In certain embodiments of the method, the pharmaceutical composition includes both of eicosapentaenoic acid, or a pharmaceutically acceptable ester thereof, and docosahexaenoic acid, or a pharmaceutically acceptable ester thereof.

In certain embodiments of the method, the pharmaceutical composition includes one of eicosapentaenoic acid, or a pharmaceutically acceptable ester thereof, and docosahexaenoic acid, or a pharmaceutically acceptable ester thereof.

In certain embodiments of the method, the pharmaceutical composition further includes one or more agents selected from the group consisting of vitamin D, vitamin C, vitamin E, vitamin B12, vitamin A, benfotiamine, chromium picolinate and vanadium.

In certain embodiments of the method, the pharmaceutically acceptable ester of eicosapentaenoic acid is an ethyl ester of eicosapentaenoic acid and the pharmaceutically acceptable ester of docosahexaenoic acid is an ethyl ester of docosahexaenoic acid.

In certain embodiments of the method, the pharmaceutical composition includes: (a) berberine, or a pharmaceutically acceptable salt thereof; (b) ethyl ester of eicosapentaenoic acid and ethyl ester of docosahexaenoic acid; and (c) a pharmaceutically acceptable excipient, carrier, or diluent.

In certain embodiments of the method, the pharmaceutically acceptable salt of berberine is a chloride salt. In certain embodiments of the method, the pharmaceutically acceptable salt of berberine is a sulfate salt.

In certain embodiments of the method, the pharmaceutical composition includes BBR and EPA/DHA at a weight ratio of BBR to EPA/DHA from about 3:1 to about 1:8 (e.g., from about 3:1 to about 1:5, from about 3:1 to about 1:3, from about 3:1 to about 1:2, from about 3:1 to about 1:1, from about 3:1 to about 2:1, from about 2:1 to about 1:8, from about 2:1 to about 1:5, from about 2:1 to about 1:2, from about 2:1 to about 1:1, from about 1:1 to about 1:8, from about 1:1 to about 1:5, from about 1:1 to about 1:3, from about 3.33:1 to about 1:3, about 3:1, about 2:1, about 1:1, about 1:2, about 1:3).

In certain embodiments, the method includes administering a unit dosage form comprising BBR in about 100 mg to about 300 mg (e.g., about 100 mg to about 250 mg, about 100 mg to about 200 mg, about 100 mg to about 150 mg, about 150 mg to about 300 mg, about 200 mg to about 300 mg, about 250 mg to about 300 mg, about 150 mg to about 250 mg) and EPA/DHA in about 100 mg to about 800 mg (e.g., about 100 mg to about 700 mg, about 100 mg to about 600 mg, about 100 mg to about 500 mg, about 100 mg to about 400 mg, about 100 mg to about 300 mg, about 100 mg to about 200 mg, about 200 mg to about 800 mg, about 300 mg to about 800 mg, about 400 mg to about 800 mg, about 500 mg to about 800 mg, about 600 mg to about 800 mg, about 700 mg to about 800 mg, about 250 mg to about 750 mg, about 500 mg to about 750 mg). In certain embodiments of the method, the unit dosage form is a soft gel capsule. In certain embodiments of the method, the unit dosage form is administered from once, twice or three times daily.

In certain embodiments of the method, the disease or disorder is selected from lipid and glucose diseases or disorders. In certain embodiments of the method, the lipid and glucose disease or disorder is selected from dyslipidemia, hyperglycemia, hypertriglyceridemia, hyperlipidemia, diabetic dyslipidemia, diabetic hyperlipidemia, dyslipidemia in statin-intolerance patients. In certain embodiments of the method, the disease or disorder is type 1 or type 2 diabetes. In certain embodiments of the method, the disease or disorder is diabetic neuropathy, diabetic nephropathy, diabetic retinopathy, or macrovascular complications comprising heart attacks, strokes or insufficiency in blood flow to legs. In certain embodiments of the method, the disease or disorder is a heart disease or atherosclerosis. In certain embodiments of the method, the disease or disorder is a neurodegenerative disease. In certain embodiments of the method, the disease or disorder is selected from fatty liver, NAFLD and NASH.

In certain embodiments of the method, treating, reducing, or preventing a disease or disorder is by reducing blood glucose levels of the subject. In certain embodiments of the method, treating, reducing, or preventing a disease or disorder is by reducing total cholesterol (TC), triglyceride (TG) and low-density lipoprotein cholesterol (LDL-c) levels, increasing high-density lipoprotein cholesterol (HDL-c) levels of the subject. In certain embodiments of the method, treating, reducing, or preventing a disease or disorder is by normalizing liver enzyme levels of the subject. In certain embodiments of the method, treating, reducing, or preventing a disease or disorder is by modulating insulin-signaling pathway such that glucose levels are reduced. In certain embodiments of the method, treating, reducing, or preventing a disease or disorder is by regulating multiple metabolic pathways such as increasing secretion of insulin, improving insulin sensitivity, reducing gluconeogenesis in liver, reducing glucose absorption, ameliorating dyslipidemia, anti-inflammation to achieve the desired pharmacological effects.

In yet another aspect, the invention generally relates to a kit including: (i) berberine, or a pharmaceutically acceptable salt thereof; (ii) one or both of eicosapentaenoic acid, or a pharmaceutically acceptable ester thereof, and docosahexaenoic acid, or a pharmaceutically acceptable ester thereof; (iii) one or more agent(s) selected from the group consisting of vitamin D, vitamin C, vitamin E, vitamin B12, vitamin A, benfotiamine, chromium picolinate and vanadium; and (iv) instructions for administering agents (i), (ii) and (iii) to a patient having or at risk of having one or more diseases or disorders selected from metabolic disorders, atherosclerosis, heart diseases, neurodegenerative diseases and liver diseases.

In certain embodiments of the kit, the pharmaceutically acceptable ester of eicosapentaenoic acid is an ethyl ester of eicosapentaenoic acid and the pharmaceutically acceptable ester of docosahexaenoic acid is an ethyl ester of docosahexaenoic acid. In certain embodiments of the kit, the pharmaceutically acceptable salt of berberine is a chloride salt. In certain embodiments of the kit, the pharmaceutically acceptable salt of berberine is a sulfate salt.

In certain preferred embodiments of the kit, the weight ratio of BBR to EPA/DHA from about 3:1 to about 1:8 (e.g., from about 3:1 to about 1:5, from about 3:1 to about 1:3, from about 3:1 to about 1:2, from about 3:1 to about 1:1, from about 3:1 to about 2:1, from about 2:1 to about 1:8, from about 2:1 to about 1:5, from about 2:1 to about 1:2, from about 2:1 to about 1:1, from about 1:1 to about 1:8, from about 1:1 to about 1:5, from about 1:1 to about 1:3, from about 3.33:1 to about 1:3, about 3:1, about 2:1, about 1:1, about 1:2, about 1:3). In certain embodiments, the kit includes about 100 mg to about 300 mg (e.g., about 100 mg to about 250 mg, about 100 mg to about 200 mg, about 100 mg to about 150 mg, about 150 mg to about 300 mg, about 200 mg to about 300 mg, about 250 mg to about 300 mg, about 150 mg to about 250 mg) of BBR and about 100 mg to about 800 mg (e.g., about 100 mg to about 700 mg, about 100 mg to about 600 mg, about 100 mg to about 500 mg, about 100 mg to about 400 mg, about 100 mg to about 300 mg, about 100 mg to about 200 mg, about 200 mg to about 800 mg, about 300 mg to about 800 mg, about 400 mg to about 800 mg, about 500 mg to about 800 mg, about 600 mg to about 800 mg, about 700 mg to about 800 mg, about 250 mg to about 750 mg, about 500 mg to about 750 mg) of EPA/DHA.

The kit may be used for treating, reducing, or preventing a disease or disorder, for example, by reducing blood glucose levels of the subject, by reducing total cholesterol (TC), triglyceride (TG) and low-density lipoprotein cholesterol (LDL-c) levels, increasing high-density lipoprotein cholesterol (HDL-c) levels of the subject, by normalizing liver enzyme levels of the subject, by modulating insulin-signaling pathway such that glucose levels are reduced, by regulating multiple metabolic pathways such as increasing secretion of insulin, improving insulin sensitivity, reducing gluconeogenesis in liver, reducing glucose absorption, ameliorating dyslipidemia, anti-inflammation to achieve the desired pharmacological effects.

the curve from the time of dosing to the time of the last observation, the $AUC_{(0-\infty)}$ represents area under the curve from the time of dosing to infinity, and the $C_{max}$ represents maximum concentration detected. The concentration-time curve and selected PK parameters are presented in Table 1 below.

TABLE 1

Select Pharmacokinetics Parameters of EPA (free acid) and BBR in SD Rats Following Single Oral Administration

| Analyte | | BBR | | | EPA (Free acid) | | |
|---|---|---|---|---|---|---|---|
| Group | Dose Level (mg/Kg) | $AUC_{(0-t)}$ μg/L*hr | $AUC_{(0-\infty)}$ μg/L*hr | $C_{max}$ μg/L | $AUC_{(0-t)}$ μg/L*hr | $AUC_{(0-\infty)}$ μg/L*hr | $C_{max}$ μg/L |
| EPA | 45.48 | — | — | — | 3750.73 | 6600.31 | 629.38 |
| BBR | 51.13 | 7.46 | 8.84 | 0.95 | — | — | — |
| BBR + EPA-EE | 51.13 + 45.48 | 28.06 | 37.46 | 6.67 | 4307.76 | 5214.47 | 635.15 |
| Vehicle | 0.5% gum tragacanth | — | — | — | 2708.52 | 7715.45 | 383.12 |

The following examples are meant to be illustrative of the practice of the invention, and not limiting in any way.

EXAMPLES

Example 1: Pharmacokinetic Properties of the Combination of Berberine and EPA/DHA in Rats and Dogs This example describes the in vivo studies in rats and dogs on the pharmacokinetic (PK) properties of the combination of berberine (BBR) and EPA and/or DHA disclosed in the present invention.

In the single-dose pharmacokinetics study in rats, after 7-day acclimation, healthy male Sprague-Dawley (SD) rats with the body weight of 210-250 g were randomized into four groups as follows (3 rats per group).

| Group | Compositions |
|---|---|
| Vehicle Control | 0.5% gum tragacanth |
| Berberine Hydrochloride (BBR•HCl) | BBR•HCl 51.13 mg/Kg |
| EPA Ethylester (EPA-EE) | EPA-EE 45.48 mg/Kg |
| BBR + EPA-EE | BBR•HCl 51.13 mg/Kg + EPA-EE 45.48 mg/Kg |

The rats in each group were orally treated with the suspensions of the corresponding testing articles indicated above in 0.5% gum tragacanth respectively. Blood samples of the test animals were collected pre-dose and at the time points of 15 min, 30 min, 1 h, 1.5 h, 2 h, 4 h, 8 h, 24 h post-dose. The collected blood samples (approximately 400 μL) were placed into tubes containing heparin sodium and centrifuged at 8,000 rpm for 6 minutes at 4° C. to separate plasma. The obtained plasma from each sample was stored at −80° C. until being analyzed.

Plasma concentrations of BBR and EPA were determined using tandem mass spectrometry (LC-MS/MS) analysis. A non-compartmental module of WinNonlin® Professional 5.2 (Pharsight; St. Louis MO), was used to calculate PK parameters. The abbreviation $AUC_{(0-t)}$ represents area under In another single-dose pharmacokinetics study in rats, after 7-day acclimation, healthy male Sprague-Dawley (SD) rats with the body weight of 210-250 g were randomized into nine groups as follows (5 rats per group).

| Group | Compositions |
|---|---|
| Vehicle Control | 0.5% gum tragacanth |
| EPA/DHA | EPA-EE/DHA-EE 100 mg/Kg |
| EPA/DHA | EPA-EE/DHA-EE 300 mg/Kg |
| EPA/DHA | EPA-EE/DHA-EE 800 mg/Kg |
| BBR | BBR•HCl 100 mg/Kg |
| BBR + EPA/DHA (1:0.3) | BBR•HCl 100 mg/Kg + EPA-EE/DHA-EE 30 mg/Kg |
| BBR + EPA/DHA (1:1) | BBR•HCl 100 mg/Kg + EPA-EE/DHA-EE 100 mg/Kg |
| BBR + EPA/DHA (1:3) | BBR•HCl 100 mg/Kg + EPA-EE/DHA-EE 300 mg/Kg |
| BBR + EPA/DHA (1:8) | BBR•HCl 100 mg/Kg + EPA-EE/DHA-EE 800 mg/Kg |

The rats in each group were orally treated with the suspensions of the corresponding testing articles indicated above in 0.5% gum tragacanth respectively. Blood samples of the test animals were collected pre-dose and at the time points of 15 min, 30 min, 1 h, 1.5 h, 2 h, 4 h, 8 h, 24 h post-dose. The collected blood samples (approximately 400 μL) were placed into tubes containing heparin sodium and centrifuged at 8,000 rpm for 6 minutes at 4° C. to separate plasma. The obtained plasma from each sample was stored at −80° C. until being analyzed.

Figure 2:
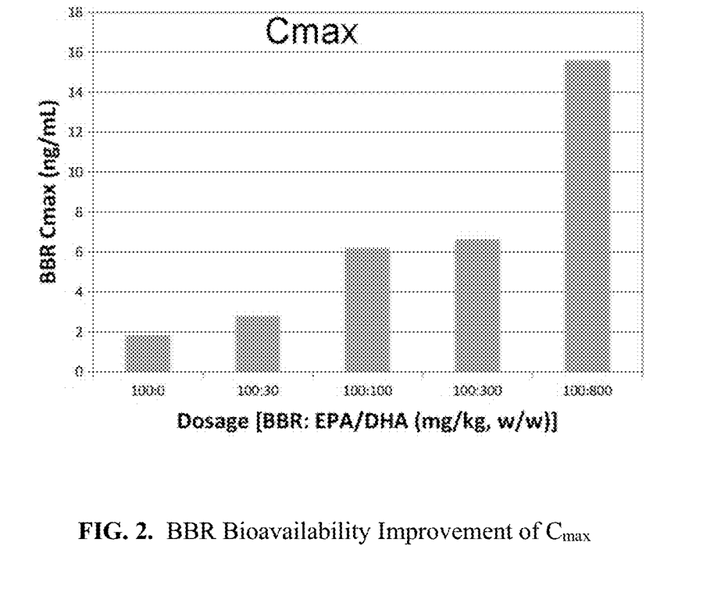
FIG. 2. BBR Bioavailability Improvement of $C_{max}$.
Figure 3:
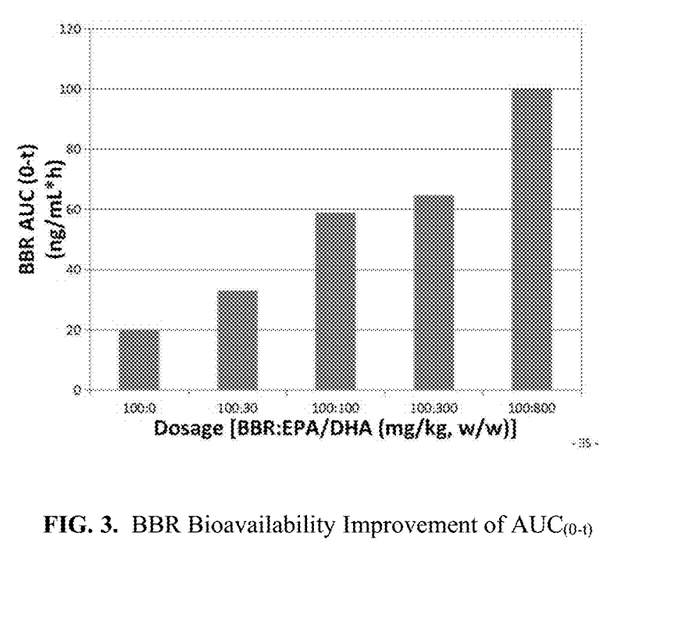
FIG. 3. BBR Bioavailability Improvement of $AUC_{(0-t)}$.
Figure 4:
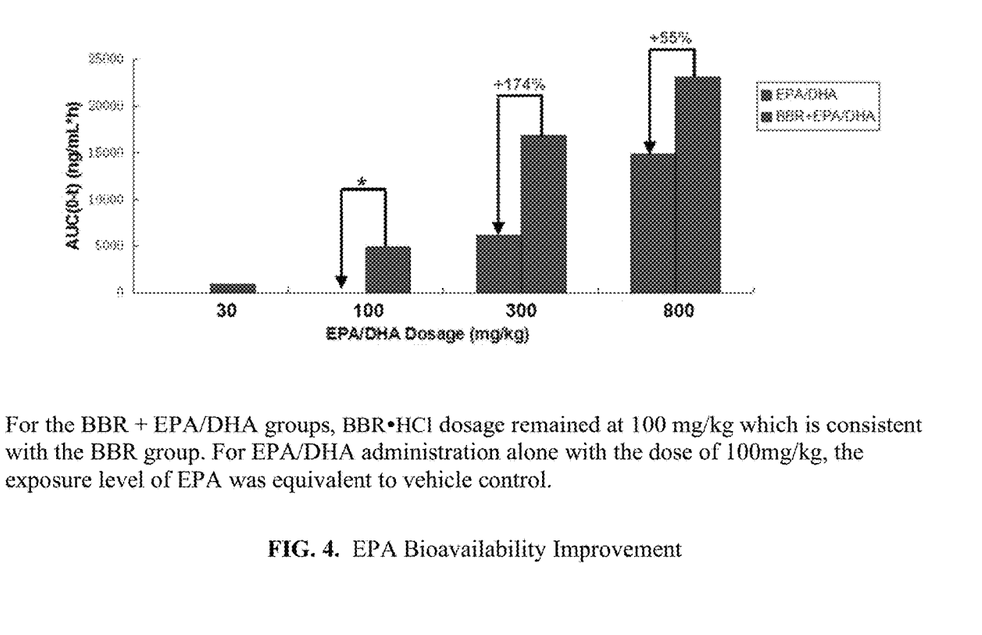
FIG. 4. EPA Bioavailability Improvement.

Plasma concentrations of BBR and EPA were determined and PK parameters were calculated. The concentration-time curve and selected PK parameters are presented in FIGS. 2-4 and Table 2 below.

TABLE 2

Selected Pharmacokinetics Parameters of BBR and EPA (free acid) in SD Rats Following Single Oral Administration

| Analyte | | BBR | | | EPA (Free acid) | | |
|---|---|---|---|---|---|---|---|
| Group | Dose Level mg/Kg | $AUC_{(0-t)}$ µg/L*hr | $AUC_{(0-\infty)}$ µg/L*hr | $C_{max}$ µg/L | $AUC_{(0-t)}$ µg/L*hr | $AUC_{(0-\infty)}$ µg/L*hr | $C_{max}$ µg/L |
| EPA/DHA | 100 | — | — | — | 8456.85 | 9563.27 | 1174.79 |
| EPA/DHA | 300 | — | — | — | 16254.39 | 19961.38 | 2384.25 |
| EPA/DHA | 800 | — | — | — | 25000.64 | 28530.44 | 4757.22 |
| BBR + EPA/DHA(1:0.3) | 100 + 30 | 49.14 | NA | 4.24 | 11045.10 | 13575.57 | 1479.70 |
| BBR + EPA/DHA(1:1) | 100 + 100 | 58.83 | 108.47 | 6.17 | 14977.86 | 22622.02 | 1935.70 |
| BBR + EPA/DHA(1:3) | 100 + 300 | 64.59 | 254.76 | 6.62 | 26970.51 | NA | 3717.06 |
| BBR + EPA/DHA(1:8) | 100 + 800 | 100.29 | 107.95 | 15.58 | 33218.55 | 27208.42 | 3967.47 |
| Vehicle | / | — | — | — | 10107.76 | 13762.89 | 1271.59 |

In the single-dose pharmacokinetics study in dogs, six healthy male beagle dogs weighing 9.95-11.45 Kg were randomized into two groups as follows (3 dogs per group).

| Group | Compositions |
|---|---|
| Hard capsule | BBR•HCl 200 mg/capsule |
| Softgel capsule | BBR•HCl 200 mg + fish oil/capsule |

The dogs in each group were orally treated with corresponding testing articles indicated above. Blood samples of the test animals were collected pre-dose and at the time points of 15 min, 30 min, 1 h, 1.5 h, 2 h, 4 h, 8 h, 24 h post-dose. Blood samples (approximately 400 µL) were collected and placed into tubes containing heparin sodium and centrifuged at 8000 rpm for 6 minutes at 4° C. to separate plasma. The obtained plasma from each sample was stored at −80° C. until being analyzed.

Figure 5:
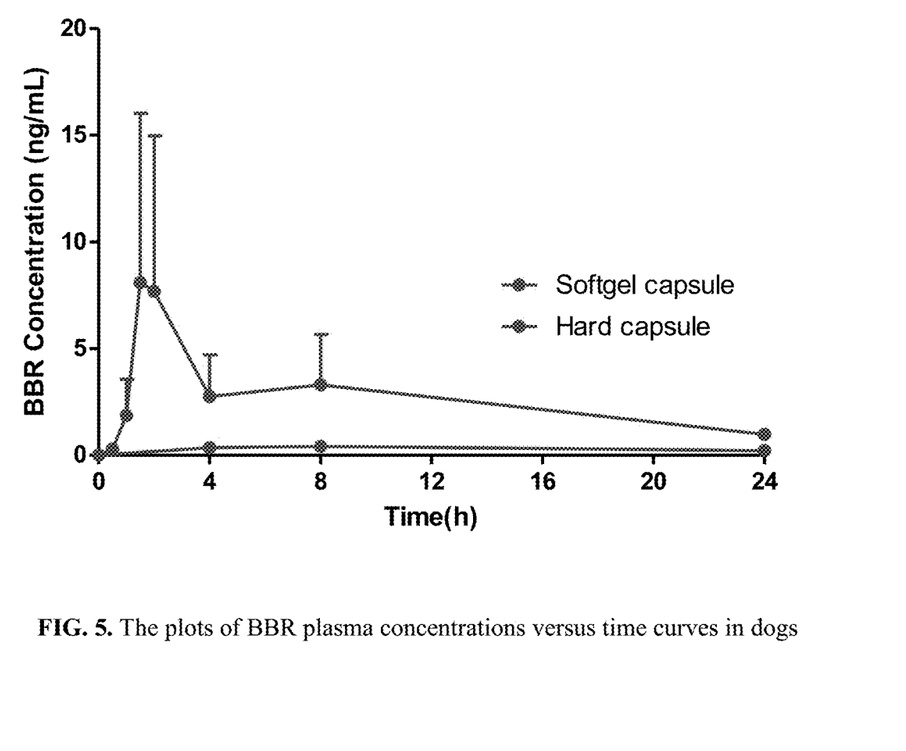
FIG. 5. The plots of BBR plasma concentrations versus time curves in dogs.

Plasma concentrations of BBR were determined and PK parameters were calculated. Following single oral administration of hard capsule (200 mg BBR/capsule), two out of three dogs' BBR plasma concentration of all collection points was below the LLOQ (0.1 ng/mL); only one dog has a measurable BBR plasma concentration with the $C_{max}$ and $AUC_{(0-24h)}$ of 0.42 ng/mL and 7.40 ng/mL*h respectively. Following single oral administration of soft gel capsule (BBR+EPA-EE/DHA-EE), the mean value of $C_{max}$ and $AUC_{(0-24h)}$ were 8.67 ng/mL and 63.42 ng/mL*h, respectively. The concentration-time curve and selected PK parameters are presented in FIG. 5 and Table 3 below.

TABLE 3

Selected Pharmacokinetics Parameters of BBR in Beagle Dogs Following Single Oral Administration

| | | BBR | | |
|---|---|---|---|---|
| Analyte | | $AUC_{(0-t)}$ | $AUC_{(0-\infty)}$ | $C_{max}$ |
| Group | Composition | µg/L*hr | µg/L*hr | µg/L |
| Softgel capsules | BBR 200 mg + fish oil | 63.42 | 173.39 | 8.67 |
| Hard capsules | BBR 200 mg | 7.4* | NA* | 0.42* |

*Only one dog has measurable BBR plasma concentration

Above experimental results indicated that comparing to BBR or EPA/DHA administering alone, the combination of BBR and EPA/DHA synergistically improve each other's bioavailability as evidenced by the increase of $C_{max}$ and AUC. In all the tested combinations with different ratios of BBR and EPA/DHA, the synergistic effect between BBR and EPA/DHA on bioavailability was observed. The increase of exposure level is impacted by the ratio of BBR and EPA/DHA; however, it is not strictly dose-dependent. The preferred ratios of BBR to EPA/DHA have been found to be in the range from about 1:1 to about 1:3.

The results demonstrate that the combination of BBR and EPA/DHA provides significantly improved pharmacokinetic properties. More specifically, in HFD/STZ induced diabetic dyslipidemia mouse model, comparing to BBR used alone, the combination of BBR and EPA/DHA has been shown to effectively: Improve glucose homeostasis; reduce TC, TG and LDL-c in serum; reduce TC, TG in liver tissue; reduce elevated liver enzymes, and improve liver function; reduce oxidative stress of liver; reduce liver index; and improve pancreas index.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples disclosed herein are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance that can be adapted to the practice of this invention in its various embodiments and equivalents thereof.

What is claimed is:

1. A softgel capsule having a unit dose of a pharmaceutical composition, wherein the pharmaceutical composition consists of:
   (a) berberine (BBR), or a chloride, sulfate or citrate salt thereof;
   (b1) eicosapentaenoic acid (EPA), or an ethyl ester thereof;
   (b2) docosahexaenoic acid (DHA), or an ethyl ester thereof; and
   (c) a pharmaceutically acceptable excipient, carrier, or diluent,
   wherein a weight ratio of the BBR to EPA and DHA is from about 3:1 to about 1:8, and the pharmaceutical composition does not contain any active agent that elicits a biological response, other than said (a), (b1) and (b2).

2. The softgel capsule of claim 1, wherein the BBR is present as a chloride, sulfate or citrate salt.

3. The softgel capsule of claim 2, wherein the EPA is present as an ethyl ester and DHA is present as an ethyl ester.

4. The softgel capsule of claim 2, wherein the BBR is a chloride salt.

5. The softgel capsule of claim 2, wherein the BBR is a sulfate salt.

6. The softgel capsule of claim 3, wherein the weight ratio of the BBR to EPA/DHA is from about 1:1 to about 1:8.

7. The softgel capsule of claim 1, wherein the unit dosage form comprises the BBR ranging from about 100 mg to about 300 mg and the EPA/DHA ranging from about 100 mg to about 800 mg.

* * * * *